Figure 1:
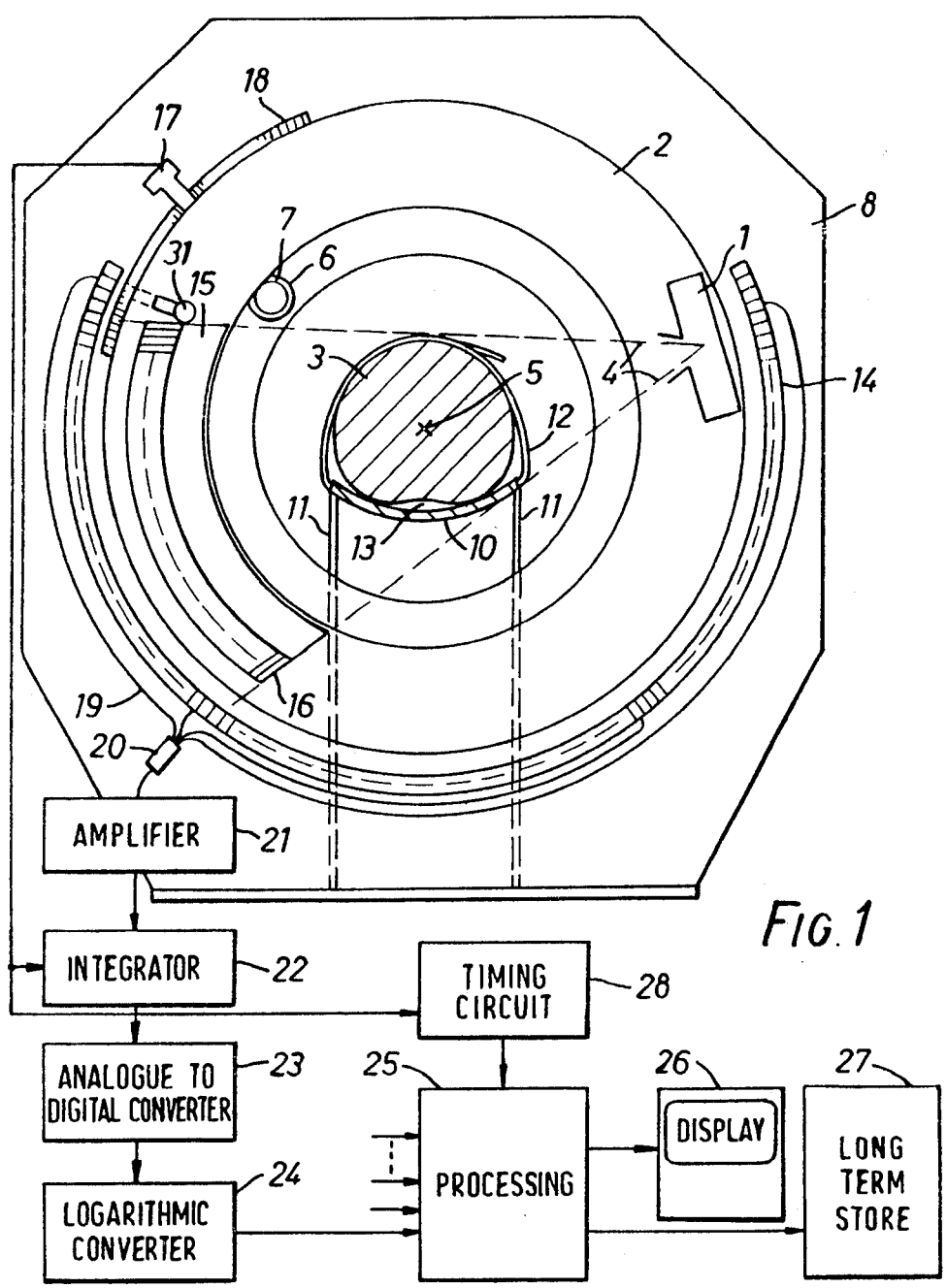

United States Patent [19]

Lill

[11] 4,101,768
[45] Jul. 18, 1978

[54] APPARATUS FOR COMPUTERIZED TOMOGRAPHY HAVING IMPROVED ANTI-SCATTER COLLIMATORS

[75] Inventor: Brian Herbert Lill, Flackwell Heath, England

[73] Assignee: EMI Limited, Hayes, England

[21] Appl. No.: 772,688

[22] Filed: Feb. 28, 1977

[30] Foreign Application Priority Data

Mar. 3, 1976 [GB] United Kingdom ................. 8417/76

[51] Int. Cl.² ........................ A61B 6/00; G01N 23/08
[52] U.S. Cl. ................................ 250/360; 250/445 T; 250/509
[58] Field of Search ................... 250/445 T, 508, 509, 250/363 S, 360

[56] References Cited

U.S. PATENT DOCUMENTS 1,542,204  6/1925  Akerlund ............................. 250/509
4,035,647  7/1977  Hounsfield et al. ............. 250/445 T

*Primary Examiner*—Alfred E. Smith
*Assistant Examiner*—T. N. Grigsby
*Attorney, Agent, or Firm*—Cooper, Dunham, Clark, Griffin & Moran.

[57] ABSTRACT

In a computerized tomographic radiographic apparatus a source of radiation projects radiation through a patient to be incident on at least some of a plurality of detector devices. To project the radiation from different directions the source moves relative to the body and also relative to the detectors to irradiate different detectors. Collimators, moving with the source, are provided to reduce the incidence of scattered radiation on the detectors. The collimators take the form of baffle plates which are arranged, to present substantially the same exit aperture to each detector despite the relative movement.

8 Claims, 4 Drawing Figures

APPARATUS FOR COMPUTERIZED TOMOGRAPHY HAVING IMPROVED ANTI-SCATTER COLLIMATORS

The present invention relates to radiography, and it relates more especially to that branch of radiography which has become known as computerises axial tomography, or briefly C.A.T. Apparatus for performing C.A.T. has the aim of evaluating the absorption coefficient, with respect to the radiation used, at each of a plurality of locations distributed over a planar slice disposed in a body under examination.

The evaluation is usually performed by suitably processing signals indicative of the absorption suffered by the radiation on traversing each of many substantially linear beam paths through the body in the plane of the slice. To obtain the required signals, it is usual to scan a source of radiation relative to the body and to detect the radiation emergent from the side of the body opposite the source whilst the source assumes many different positions relative to the body, as described in one example given in U.S. Pat. No. 3,778,614.

If it is desired to acquire the signals rapidly, it is convenient to use a source of a fan-shaped, planar spread of radiation which emcompasses at least a substantial part of the slice; the planes of the spread of radiation and of the slice being conincident. Such a spread may be a continuous fan of radiation or may if desired be split up by collimators between the body and the source. An array of detector devices is disposed at the opposite side of the body to the source so that each detects the radiation emergent from the body along a respective beam path, the paths being divergent, and the source and the detector devices are rotated around the body about a common axis substantially perpendicular to the planes of the slice and of the spread of radiation, so as to provide signals relating to the absorption suffered by the radiation on traversing further groups of beam paths; signals relating to many groups of beam paths being obtained on rotation of the source and the detector devices through for example an angle exceeding 180° by about the angle of the fan of radiation. Such a technique is described and claimed in United States Application No. 481,443. Preferably the signals are sorted into sets relating to substantially parallel beam paths and are processed, a set at a time, by the technique disclosed and claimed in U.S. Pat. No. 3,924,129, due allowance being made for the fact that the parallel beam paths are not uniformly spaced across the slice. U.S. Pat. No. 3,778,614 and United States application No. 481,443 and U.S. Pat. 3,924,129 are hereby incorporated herein by reference. It will be understood that the data need not be sorted into sets of parallel beam paths provided processing appropriate to fan distributions of beam paths is used.

A difficulty arises, however, due to the tendency of different detector devices to drift in gain relative to one another during the time taken to acquire the signals, i.e., the scanning time. Since in an apparatus using only or primarily a rotary scanning motion a given detector always provides signals relating to beam paths at a constant or substantially constant perpendicular distance from the axis of rotation, such drifting causes the superposition of ring-shaped artifacts upon the evaluated coefficients.

It is an object of this invention to reduce the above-mentioned difficulty.

According to the invention there is provided radiographic apparatus including a source adapted to project a fan-shaped spread of penetrating radiation through a slice of the body of a patient, means for causing said source to effect at least an angular movement, relative to the body, about an axis intersecting the slice so as to project the radiation through the body from a plurality of directions, a plurality of detector devices disposed to receive the radiation after projection through the body and a plurality of plates disposed between the body and the detector devices to reduce the incidence, on detector devices being irradiated, of radiation transmitted from said souce along indirect paths, wherein said source and said plates are arranged to move relative to said detector devices, the arrangement being such that said plates present substantially the same exit aperture to each detector device despite the relative movement.

Figure 2A:
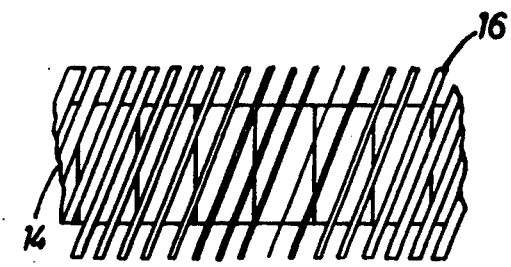
Figure 2B:
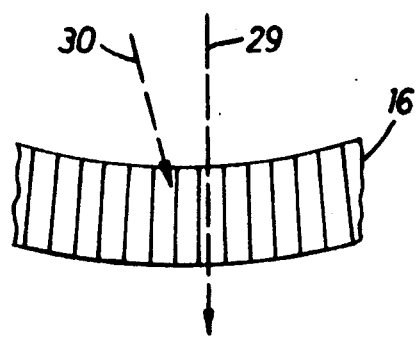
Figure 3:
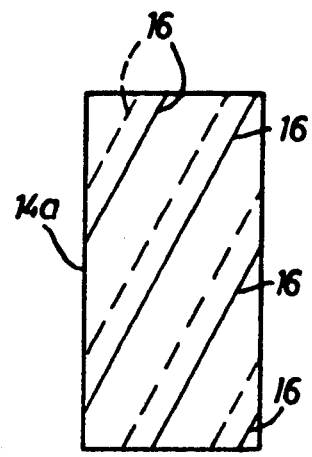

In order that the invention may be clearly understood and readily carried into effect, one embodiment thereof will now be described, by way of example only, with reference to the accompanying drawings of which FIG. 1 shows, in schematic front elevational view, apparatus in accordance with one example of the invention, FIGS. 2a and 2b show the relationship of collimator baffle plates to the detector devices, and FIG. 3 is a diagram used to explain the principles of the collimator baffle plates.

Referring to the drawing, an X-ray tube 1, typically a rotating anode tube of conventional construction, is mounted on an angularly movable ring 2 so as to irradiate a part 3 of a patient's body. The tube 1 is arranged to produce a substantially planar, fan-shaped spread 4 of X-radiation, and the body is positioned so that the part 3, which represents a cross-sectional slice over which the absorption coefficients are to be evaluated is in the plane of the spread 4. The angular motion of the ring 2 occurs about an axis 5 which is disposed, in this example, substantially centrally of the body part 3 and is perpendicular to the plane of the spread 4. The motive force for effecting the angular movement of the ring 2 is an electric motor 6 which drives a gear wheel 7. The latter co-operates with gear teeth formed all around the inner periphery of the ring 2. Motor 6 is mounted on a stationary main frame 8 concentric with the ring 2 and sufficiently large to enable the body to pass therethrough in a supine position. The body is supported on a bed 10, which itself is supported as at 11 on either side of the scanning gantry, and secured thereto by means of strap 12. Packing material 13, which may contain water or viscous or particulate material in one or more plastic bags, is placed between the body and the bed 10 in the region of examination so as to reduce the entrapment of air between the body part 3 and the bed 10. The material 13 preferably absorbs the X-radiation to a similar extent as does human tissue.

The main frame 8 also supports a bank 14 of detector devices; the devices being disposed on a circular path concentric with, but of larger radius than, the ring 2, i.e., centred on axis 5. The array extends over an angle which, in this example, substantially equals the sum of 180° and the fan angle. Since the angle of the fan-shaped spread 4 of radiation is 40° in this example, the extent of the detector array 14 is approximately 220°. This extent is necessary in order that signals may be obtained relating to sets containing equal numbers of parallel beam paths distributed over substantially 180° as is required for highly accurate operation if the signals are to be processed in accordance with the technique described and claimed in the aforementioned U.S. Pat. No. 3,924,129. If desired the detector array may extend over the full 360°.

Each detector device in the array 14 typically comprises a scintillator crystal, for example thallium activated caesium iodide, together with a light sensitive element such as a photomultiplier tube or a photo diode. Between the detector array 14 and the body is disposed a collimator arrangement 15, 16, to reduce scatter incident upon the detector devices. The element 15 of the collimator arrangement comprising a pair of plates disposed parallel to the plane of the spread 4 of radiation and the element 16 comprising a baffle consisting of a plurality of collimator plates which are parallel to one another in one direction and inclined to the junction lines between adjacent detector crystals as will be explained in more detail hereinafter. The baffle 16, while reducing the amount of incident scattered radiation, does not define a precise angle of incidence for each individual detector. This enables the detector devices to receive radiation projected along various beams within the spread 4 as the radiation is scanned over the devices during the angular movement of the ring 2. The pitch of the baffle plates is not necessarily related to the distance between corresponding parts of adjacent detector devices, however it is typically of the same magnitude as or less than the detector pitch.

The detector devices in some parts of the array 14 have to be capable of receiving radiation from any angle within the spread 4 and thus each detector is arranged to view the source through an aperture having a 40° field of view.

It will be appreciated that allowance has to be made, in determining the placing of the detector devices, for the fact that the circular path upon which the detector devices are located is of larger diameter than the trajectory of the effective point source of radiation. In one example, 660 detectors are provided, angularly spaced by $\frac{1}{3}°$ in relation to axis 5.

In operation, the active scan commences with the fan in a position to irradiate a group of detectors at one extreme of array 14 and the ring 2, and with it the source 1, is angularly moved around the body part 3 about axis 5. Clearly, as the angular movement proceeds, the radiation sweeps around the detector array 14; the output signals provided by the devices of array 14 being sampled at a rate determined by timing pulses produced by the co-operation of a photocell unit 17, mounted on the stationary frame 8, and a graticule 18 mounted on the ring 2. At regular intervals one detector device at the rear end of the spread 4 is substituted by a new detector device at the forward end of the spread 4, so that samples are at all times provided by the same number of detectors. In order to save expense, detectors spaced apart by more than the fan angle, i.e., detectors which cannot be irradiated at the same time, can share photomultipliers and/or subsequent electrical circuits on a time division basis. The scan is terminated when all detectors have been irradiated by radiation which has passed through the body.

Such an arrangement is shown in the drawing; detectors spaced apart in angle by more than 40° being coupled, via fiber-optic light guides such as 19 to a common photomultiplier such as 20 and each photomultiplier being arranged to feed a respective channel comprising an amplifier such as 21, an integrator such as 22 which is read and reset periodically by the aforementioned timing pulses, an analogue to digital converter circuit such as 23 and a logarithmic converter circuit such as 24. All of the logarithmic converter circuits such as 24 feed a processing circuit 25 which is arranged to sort the signals applied thereto into sets relating to parallel beam paths through the body part 3, to adjust the signals to take account of the aforementioned non-uniformity of spacing of the parallel beam paths and to process the signals so sorted and adjusted in accordance with the technique described and claimed in the aforementioned patent application to evaluate the absorption coefficient at each of a plurality of locations distributed over the slice comprising the body part 3. Preferably the coefficients so evaluated are displayed on a visual display such as a cathode ray tube 26, which has facilities for photographing the display thereon, and also supplied to a long term store 27. Store 27 is preferably a magnetic tape or disc store. The time division multiplexing of the various photomultipliers and subsequent channels of electrical circuits is effected under the influence of a timing circuit 28 which receives the aforementioned timing pulses and develops further timing signals which operate gates in the circuit 25 to route the various signals to their correct locations.

The arrangement of the baffles 16 is shown schematically in plan view in FIG. 2a and, in the same elevation as FIG. 1, in FIG. 2b. Part of the detector array 14 is also shown. As in FIG. 1, the baffles and detectors are each disposed on circles centred on the axis 5 and the junctions between individual detectors are on radii from that axis. The baffles 16 are, however, radial to the origin of the X-rays so that they intercept directly transmitted radiation as little as possible. For the same reason they are relatively thin. In this way they allow direct radiation, such as 29, to pass to the detectors with little loss but tent to intercept scattered radiation, such as 30. The junction between individual detectors is intended to include a plane lying midway between adjacent detectors which may not be in actual physical contact.

It is nevertheless not possible to prevent the baffles 16 intercepting at least some radiation directly transmitted from the source. Furthermore the baffles 16, in the course of rotation about axis 5, move relative to the detectors 14. If the output readings from each detector are to be of equal significance it is necessary to ensure that each detector loses the same proportion of radiation, to any baffles disposed in its path, in each sampling period of an integrator. Clearly, for baffles parallel to the junctions between detectors (i.e., in a direction perpendicular to the paper in FIG. 2b), the timing of the integrators must be carefully regulated to achieve that effect. In certain circumstances an error of timing equivalent to a circumferential movement of the thickness of one baffle plate could lead to an error which may be unacceptable.

Figure 2B:
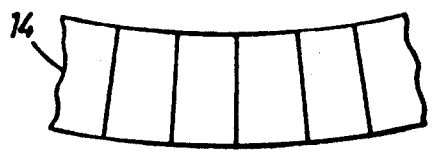

The arrangement of FIG. 2 therefore disposes the baffles 16 so that they are inclined to the junctions between detectors in the said direction. The amount of baffle overlying each detector during an integration period is then constant, despite timing errors, provided that the inter baffle spacing is not too large.

FIG. 3 illustrates the relationship for one detector crystal 14a, which is shielded by several baffles 16 to the extent indicated by the solid lines. If the baffles move relative to the detector to the position indicated by the broken lines it can be seen that the total baffle length, shielding the detector, is substantially the same.

It will be understood that other shapes and dispositions of baffles may be used, for example s-shaped or chevron-shaped, provided the baffles present substantially the same exit aperture for the radiation to each detector device despite their relative movement. That effect requires that when the proportion of any baffle overlying a detector device increases, the overlying proportion of another baffle should decrease to substantially the same extent. The pitch of the baffle must be sufficiently short to give that effect.

Of course baffles may be disposed parallel to the junction lines between detectors of the integrator timing is precisely controlled as indicated hereinbefore.

As the fan-shaped spread 4 of radiation is more than sufficient to embrace the breadth of the body part 3 in the examination plane, each detector receives, at least once during the examination, radiation directly from the source 1. The output signals obtained at these times are used as calibration signals to check the sensitivity of the detectors.

If the body is too large in some or all dimensions to permit the calibration referred to above to be effected for all detector devices, an auxiliary source 31 can be mounted on the ring 2 beyond one extreme of the fan of radiation and used to irradiate the detector devices directly (i.e., not through the body) to enable calibration signals to be obtained. The auxiliary source 31 may be an X-ray tube or a radioisotope source and may project radiation at the detector devices along a single pencil-like beam or along a fan-like spread. It is, of course, necessary to take account of the presence of the auxiliary source when deciding which detector devices can share photomultipliers etc. If necessary, the auxiliary radiation can be of differnt energy distribution than the main source 1 so that information relating to the two sources, if fed into a common chanel, can be separated on an energy basis, such separation being well known in the art.

In a further embodiment of the invention more than one X-ray source such as 1 may be provided to irradiate the entire detector array in the course of a lesser angular motion.

What I claim is:

1. Radiographic apparatus including a source adapted to project a fan-shaped spread of penetrating radiation through a slice of the body of a patient, means for causing said source to effect at least an angular movement, relative to the body, about an axis intersecting the slice so as to project the radiation through the body from a plurality of directions, a plurality of detector devices disposed to receive the radiation after projection through the body and a plurality of plates disposed between the body and the detector devices to reduce the incidence, on detector devices being irradiated, of radiation transmitted from said source along indirect paths, wherein said source and said plates are arranged to move relative to said detector devices, the arrangement being such that said plates present substantially the same exit aperture to each detector device despite the relative movement.

2. Apparatus according to claim 1 wherein the detector devices are disposed so that the junctions between adjacent detectors are parallel in the direction of the axis and the said plates are disposed in planes which are parallel in a direction inclined to the direction of the axis.

3. Apparatus according to claim 1 wherein the detector devices are disposed along a circular path centred on the axis so tht planes defined by the junctions between adjacent detectors intersect at the axis and the said plates are disposed on a further circular path centred on the axis at a smaller radius therefrom but lying in respective planes which interect at the source.

4. A radiographic apparatus including: a source adatped to project a fan-shaped spread of penetrating radiation through a slice of the body of a patient; means for angularly moving the source relative to the body about an axis, intersecting the slice, as to project the radiation through the body from a plurality of directions; detector means arranged to measure the intensity of the radiation after passage through the body, comprising a plurality of detector devices disposed in sequence so that the junctions between adjacent detector devices are substantially parallel to the said axis; a plurality of planar baffle plates disposed between the body and the sequence of detector devices and arranged so that their planes intersect, substantially at the source, at a line inclined to the direction of the said axis, the pitch of the plates relative to the detector spacing being such that the plates present substantially the same exit aperture to each detector irradiated for any relative position therebetween.

5. An apparatus according to claim 4 wherein the detector devices are disposed along a circular path centred on said axis and the baffle plates are disposed along a further circular path centred on said axis at a smaller radius than the first mentioned circular path.

6. A medical diagnostic apparatus for examining a slice of a patient with penetrating radiation, comprising:
    means for irradiating the patient with a substantially planar, fan-shaped spread of the penetrating radiation which originates at a location orbiting around the patient and propagates through the patient along beam paths which intersect in the patient and travel along or substantially along the plane of the slice;
    detectors of the penetrating radiation disposed to receive radiation exiting the patient along said different beam paths; and
    collimators disposed between the patient and the detectors in the path of the spread of radiation, said collimators moving with respect to the detectors and shading from radiation along said beam paths, at any one time, substantially the same area of each detector receiving radiation along said beam paths despite the relative movement between the collimators and the detectors.

7. A medical diagnostic apparatus as in claim 6 wherein said collimators comprise a plurality of spaced apart plates extending along planes which intersect substantially at the origin of the radiation.

8. A medical radiographic apparatus as in claim 7 wherein the detectors are disposed in a row extending along the plane of said spread of radiation and each collimator plate is at an angle to said plane which is substantially different from 90° and 180°.

* * * * *